(12) United States Patent
Sherman et al.

(10) Patent No.: US 7,497,837 B2
(45) Date of Patent: *Mar. 3, 2009

(54) CHEST COMPRESSION DEVICE WITH ELECTRO-STIMULATION

(75) Inventors: Darren R. Sherman, Portola Valley, CA (US); Steven R. Bystrom, Portola Valley, CA (US)

(73) Assignee: Zoll Circulation, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/374,855

(22) Filed: Mar. 13, 2006

(65) Prior Publication Data

US 2006/0155222 A1    Jul. 13, 2006

Related U.S. Application Data

(63) Continuation of application No. 10/648,007, filed on Aug. 25, 2003, now Pat. No. 7,011,637, which is a continuation of application No. 09/829,859, filed on Apr. 9, 2001, now abandoned, which is a continuation of application No. 09/100,840, filed on Jun. 19, 1998, now Pat. No. 6,213,960.

(51) Int. Cl.
*A61H 31/00* (2006.01)

(52) U.S. Cl. ............... 601/41; 601/DIG. 6; 601/DIG. 9; 601/DIG. 10

(58) Field of Classification Search ............ 601/41–44, 601/107, 108, 152, DIG. 8, DIG. 9, DIG. 10; 607/3–5
See application file for complete search history.

(56) References Cited

U.S. PATENT DOCUMENTS

| | | | |
|---|---|---|---|
| 2,071,215 A | 2/1937 | Petersen | 128/28 |
| 2,699,163 A | 1/1955 | Engstrom | 128/29 |
| 2,754,817 A | 7/1956 | Nemeth | 128/60 |
| 2,780,222 A | 2/1957 | Polzin et al. | 128/30 |
| 2,853,998 A | 9/1958 | Emerson | 128/30 |
| 2,899,955 A | 8/1959 | Huxley, III et al. | 128/30 |
| 3,042,024 A | 7/1962 | Mendelson | 128/30 |
| 3,120,228 A | 2/1964 | Huxley, III | 128/30 |
| 3,368,550 A | 2/1968 | Glascock | 128/2 |
| 3,461,860 A | 8/1969 | Barkalow et al. | 128/53 |

(Continued)

OTHER PUBLICATIONS

Tortora, et al., *Principles of Anatomy and Physiology*, Harper Collins, pp. 296 and 378, Aug. 2003.

*Primary Examiner*—Danton DeMille
(74) *Attorney, Agent, or Firm*—K. David Crockett, Esq.; Paul J. Backofen, Esq.; Crockett & Crockett

(57) ABSTRACT

A device for performing chest compressions for CPR in coordination with applying electro-stimulus for additional resuscitative actions such as electro-ventilation, electro-counterpulsion, and defibrillation. The device includes a chest compression mechanism, electrodes and power supply for electro-stimulus, and a control system for applying electro-stimulus in coordination with the action of the chest compression mechanism.

10 Claims, 5 Drawing Sheets

U.S. PATENT DOCUMENTS

| | | | |
|---|---|---|---|
| 3,481,327 A | 12/1969 | Drennen | 128/30.2 |
| 3,610,233 A * | 10/1971 | Barkalow | 601/106 |
| 3,782,371 A | 1/1974 | Dorouineau | 128/28 |
| 4,198,963 A * | 4/1980 | Barkalow et al. | 601/106 |
| 4,273,114 A | 6/1981 | Barkalow et al. | 128/53 |
| 4,349,015 A | 9/1982 | Alferness | 128/28 |
| 4,397,306 A | 8/1983 | Weisfeldt et al. | 128/28 |
| 4,570,615 A | 2/1986 | Barkalow | 128/28 |
| 4,664,098 A | 5/1987 | Woudenberg et al. | 128/53 |
| 4,770,164 A * | 9/1988 | Lach et al. | 601/41 |
| 4,827,935 A | 5/1989 | Geddes | 128/419 |
| 4,907,602 A | 3/1990 | Sanders | 128/787 |
| 4,915,095 A | 4/1990 | Chun | 128/28 |
| 4,928,674 A * | 5/1990 | Halperin et al. | 601/44 |
| 5,014,698 A | 5/1991 | Cohen | 607/4 |
| 5,056,505 A | 10/1991 | Warwick et al. | 128/30.2 |
| 5,078,134 A | 1/1992 | Heilman et al. | 607/4 |
| 5,098,369 A | 3/1992 | Heilman et al. | 600/16 |
| 5,184,606 A | 2/1993 | Csorba | 128/28 |
| 5,184,620 A | 2/1993 | Cudahy et al. | 600/382 |
| 5,190,036 A | 3/1993 | Linder | 128/421 |
| 5,217,010 A | 6/1993 | Tsitlik et al. | 128/419 |
| 5,222,478 A | 6/1993 | Scarberry et al. | 128/30.2 |
| 5,257,619 A | 11/1993 | Everete | 128/28 |
| 5,277,194 A | 1/1994 | Hosterman et al. | 128/721 |
| 5,284,135 A | 2/1994 | Lopin | 607/4 |
| 5,295,481 A | 3/1994 | Geeham | 601/43 |
| 5,327,887 A | 7/1994 | Nowakowski | 128/204.21 |
| 5,359,999 A | 11/1994 | Kinsman | 128/204.21 |
| 5,370,603 A | 12/1994 | Newman | 601/41 |
| 5,397,337 A | 3/1995 | Jaeger et al. | 607/62 |
| 5,399,148 A | 3/1995 | Waide et al. | 601/41 |
| 5,405,362 A | 4/1995 | Kramer | 607/5 |
| 5,411,031 A | 5/1995 | Yomtov | 600/519 |
| 5,474,533 A | 12/1995 | Ward et al. | 604/26 |
| 5,490,820 A | 2/1996 | Schock et al. | 601/41 |
| 5,630,789 A | 5/1997 | Schock et al. | 601/41 |
| 5,664,563 A | 9/1997 | Schroeder et al. | 128/204.25 |
| 5,716,380 A | 2/1998 | Yerkovich et al. | 607/2 |
| 5,738,637 A * | 4/1998 | Kelly et al. | 601/41 |
| 5,755,756 A | 5/1998 | Freedman, Jr. et al. | 607/110 |
| 5,814,086 A | 9/1998 | Hirschberg et al. | 607/14 |
| 5,833,711 A | 11/1998 | Schneider, Sr. | 607/3 |
| 6,234,985 B1 | 5/2001 | Lurie et al. | 601/41 |

* cited by examiner

CHEST COMPRESSION DEVICE WITH ELECTRO-STIMULATION

This application is a continuation of U.S. application Ser. No. 10/648,007, filed Aug. 25, 2003, now U.S. Pat. No. 7,011,637 which is a continuation of U.S. application Ser. No. 09/829,859, filed Apr. 9, 2001, now abandoned, which is a continuation of U.S. application Ser. No. 09/100,840, filed Jun. 19, 1998, now U.S. Pat. No. 6,213,960.

FIELD OF THE INVENTIONS

This invention relates to the resuscitation of cardiac arrest victims.

BACKGROUND OF THE INVENTIONS

Cardiopulmonary resuscitation (CPR) is a well known and valuable method of first aid. CPR is used to resuscitate people who have suffered from cardiac arrest after heart attack, electric shock, chest injury and many other causes. During cardiac arrest, the heart stops pumping blood, and a person suffering cardiac arrest will soon suffer brain damage from lack of blood supply to the brain. Thus, CPR requires repetitive chest compression to squeeze the heart and the thoracic cavity to pump blood through the body. Very often, the victim is not breathing, and mouth to mouth artificial respiration or a bag valve mask is used to supply air to the lungs while the chest compression pumps blood through the body. The methods of providing oxygenated airflow to the lungs are referred to as ventilation.

It has been widely noted that CPR and chest compression can save cardiac arrest victims, especially when applied immediately after cardiac arrest. Chest compression requires that the person providing chest compression repetitively push down on the sternum of the victim at 80-100 compressions per minute. CPR and closed chest compression can be used anywhere, wherever the cardiac arrest victim is stricken. In the field, away from the hospital, CPR may be accomplished by ill-trained by-standers or highly trained paramedics and ambulance personnel.

When a first aid provider performs chest compression well, blood flow in the body is typically about 25-30% of normal blood flow. This is enough blood flow to prevent brain damage. However, when chest compression is required for long periods of time, it is difficult if not impossible to maintain adequate compression of the heart and rib cage. Even experienced paramedics cannot maintain adequate chest compression for more than a few minutes. Hightower, et al., Decay In Quality Of Chest Compressions Over Time, 26 Ann. Emerg. Med. 300 (September 1995). Thus, long periods of CPR, when required, are not often successful at sustaining or reviving the victim. At the same time, it appears that, if chest compression could be adequately maintained, cardiac arrest victims could be sustained for extended periods of time. Occasional reports of extended CPR efforts (45-90 minutes) have been reported, with the victims eventually being saved by coronary bypass surgery. See Tovar, et al., Successful Myocardial Revascularization and Neurologic Recovery, 22 Texas Heart J. 271 (1995).

In efforts to provide better blood flow and increase the effectiveness of bystander resuscitation efforts, modifications of the basic CPR procedure have been proposed and used. Various devices and methods described below are proposed for use in a main operative activity of CPR, namely repetitive compression of the thoracic cavity. The device shown in Barkalow, Cardiopulmonary resuscitator Massager Pad, U.S. Pat. No. 4,570,615 (Feb. 18, 1986), the commercially available Thumper device, and other such devices, provide continuous automatic closed chest compression. Barkalow and others provide a piston which is placed over the chest cavity and supported by an arrangement of beams. The piston is placed over the sternum of a patient and set to repeatedly push downward on the chest under pneumatic power. The victim must first be installed into the device, and the height and stroke length of the piston must be adjusted for the patient before use, leading to delay in chest compression. Other analogous devices provide for hand operated piston action on the sternum. Everette, External Cardiac Compression Device, U.S. Pat. No. 5,257,619 (Nov. 2, 1993), for example, provides a simple chest pad mounted on a pivoting arm supported over a patient, which can be used to compress the chest by pushing down in the pivoting arm. These devices are not clinically more successful than manual chest compression. See Taylor, et al., External Cardiac Compression, A Randomized Comparison of Mechanical and Manual Techniques, 240 JAMA 644 (August 1978). Other devices for mechanical compression of the chest provide a compressing piston which is secured in place over the sternum via vests or straps around the chest. Woudenberg, Cardiopulmonary Resuscitator, U.S. Pat. No. 4,664,098 (May 12, 1987) shows such a device which is powered with an air cylinder. Waide, et al., External Cardiac Massage Device, U.S. Pat. No. 5,399,148 (Mar. 21, 1995) shows another such device which is manually operated.

Lach, et al., Resuscitation Method and Apparatus, U.S. Pat. No. 4,770,164 (Sep. 13, 1988) proposed compression of the chest with wide band and chocks on either side of the back, applying a side-to-side clasping action on the chest to compress the chest. Kelly, et al., Chest Compression Apparatus for Cardiac Arrest, U.S. Pat. Nos. 5,738,637 (5,738,673) proposed compression of the chest using a wide band repeatedly tightened about the chest with a lever assembly placed on the patients sternum and operated manually. The Kelly devices comprises a base which is placed over a central region of the chest, a belt which is wrapped around the patients chest and fastened at its opposite ends to the base, and a force converter connected to the base and the belt, and a manual actuator, so that the force converter converts the downward force on the manual actuators into chest compressing resultants directed toward the chest and directed tangentially to the chest. Although Kelly illustrates installation of defibrillation electrodes on the wide band, he does not suggest integrating use of the electrodes with use of the compression belt in any manner.

In another variation of such devices, a vest or belt designed for placement around the chest is provided with pneumatic bladders which are filled to exert compressive forces on the chest. Scarberry, Apparatus for Application of Pressure to a Human Body, U.S. Pat. No. 5,222,478 (Jun. 29, 1993) and Halperin, Cardiopulmonary Resuscitation and Assisted Circulation System, U.S. Pat. No. 4,928,674 (May 29, 1990) show examples of such devices. Halperin, for example, uses a vest fitted with air bladders that are repeatedly inflated to compress the chest. The bladders are deflated by application of a vacuum. Cyclic inflation and deflation of the vest is accomplished with a complicated arrangement of two-way and three-way valves, connected to the bladders within the vest with large bore hoses.

Our own CPR devices use a compression belt around the chest of the patient which is repetitively tightened and relaxed through the action of a belt tightening spool powered by an electric motor. The motor is controlled by control system which times the compression cycles, limits the torque applied by the system (thereby limiting the power of the compression applied to the victim), provides for adjustment of the torque limit based on biological feedback from the patient, provides for respiration pauses, and controls the compression pattern through an assembly of clutches and/or brakes connecting the motor to the belt spool. Our devices have achieved high levels of blood flow in animal studies.

Abdominal binding is a technique used to enhance the effectiveness of the CPR chest compression. Abdominal binding is achieved by binding the stomach during chest compression to limit the waste of compressive force which is lost to deformation of the abdominal cavity caused by the compression of the chest. It also inhibits flow of blood into the lower extremities (and promotes bloodflow to the brain). Alferness, Manually-Actuable CPR apparatus, U.S. Pat. No. 4,349,015 (Sep. 14, 1982) provides for abdominal restraint during the compression cycle with a bladder that is filled during compression. Counterpulsion is a method in which slight pressure is applied to the abdomen in between each chest compression. A manual device for counterpulsion is shown in Shock, et al., Active Compression/Decompression Device for Cardiopulmonary Resuscitation, U.S. Pat. No. 5,630,789 (May 20, 1997). This device is like a seesaw mounted over the chest with a contact cup on each end of the seesaw. One end of the seesaw is mounted over the chest, and the other end is mounted over the abdomen, and the device is operated by rocking back and forth, alternately applying downward force on each end.

Electroventilation is the process of ventilating a patient. by electrically stimulating the nerves that control the muscles used for respiration. It is proposed for use in patients that have been paralyzed such that the normal motor impulses transmitted to the diaphragm are not transmitted. Geddes, Demand Electroventilator, U.S. Pat. No. 4,827,935 (May 9, 1989) illustrates the operation of an electroventilator. He illustrates placement of two electrodes on the chest (one on either side), and application of electrical stimulus through the electrodes to stimulate the nerves responsible for triggering the muscles used in respiration. Geddes system provided for smooth inspiration, which was an improvement over the sharp gasping action caused by earlier electroventilation systems. The nerves identified by Geddes are the phrenic nerve, which controls the diaphragm, and the intercostal nerves which control the intercostal muscles (muscles between the ribs).

SUMMARY

The devices and methods described below combine mechanisms for compressing the chest with electrical devices for conducting other beneficial components of cardiopulmonary resuscitation and the ACLS protocol. A set of electrodes is provided on the neck and/or chest of the patient for electrically stimulating the diaphragm to provide an inhalation, thereby ventilating the patient, and a control system provides for coordination of the ventilating stimulus with the compression system so that ventilation is initiated during ventilation pauses in the compression pattern (these compression pauses would normally be used for mouth-to-mouth or bag ventilation). A set of electrodes is provided for installation over the patient's abdomen, to cause contraction of the abdominal muscles, and a control system provides for coordination of the abdominal muscle stimulation and the chest compression mechanism in order to effect abdominal binding or counterpulsion. A set of electrodes is provided for defibrillating the patient, and a control system is provided for coordinating the initiating the defibrillation shock in sync with the chest compression mechanism. The defibrillation electrodes may be used for pacing the heart. Additional electrodes may be supplied for control of the glottic opening. An overall control system is provided for coordinating the action of the chest compression device with the operation of various electrical stimulus devices to enhance the effectiveness of the resuscitation regimen.

DETAILED DESCRIPTION OF THE INVENTIONS

Figure 1:
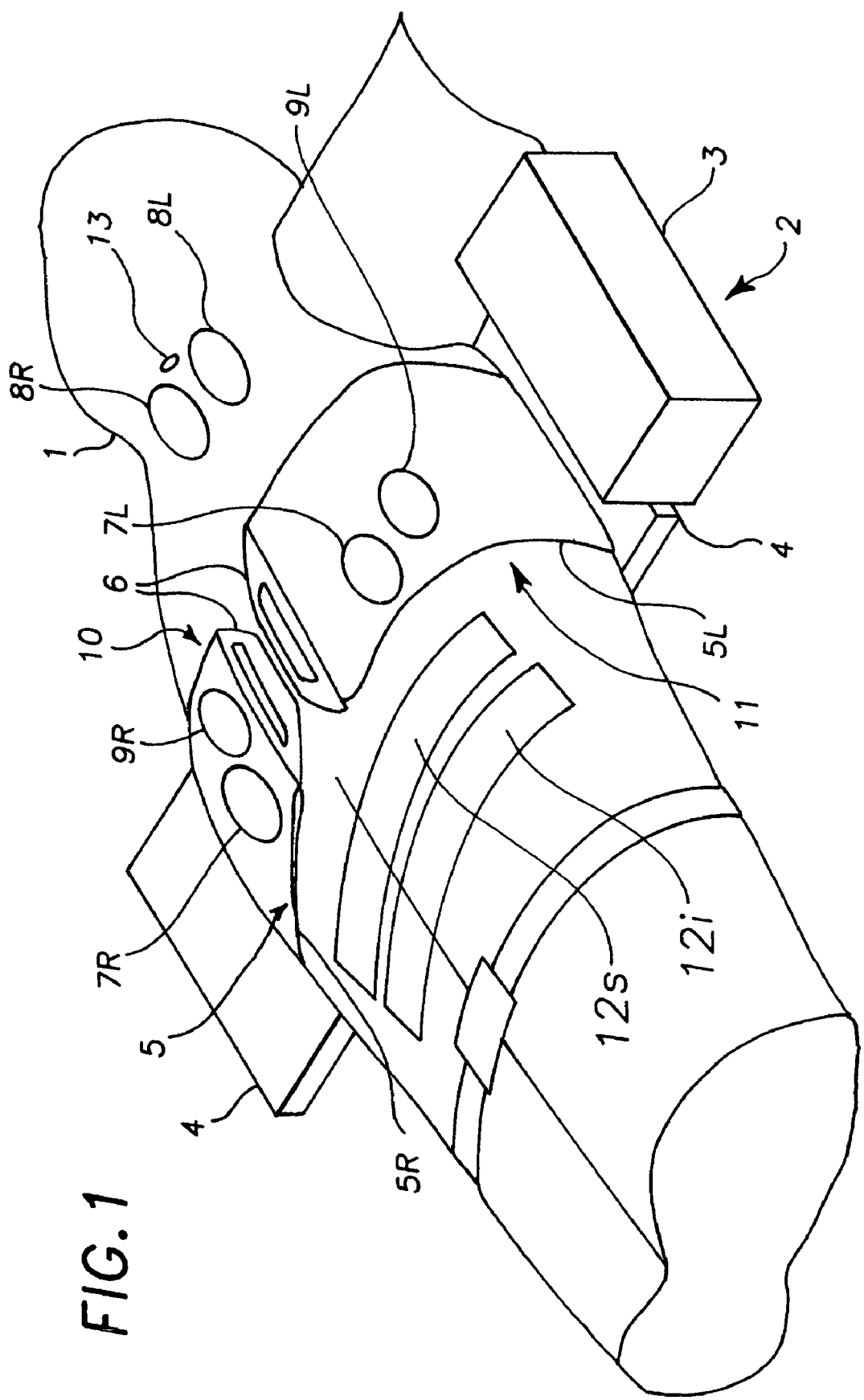
FIG. 1 is diagram of a typical chest compression device.

FIG. 1 shows the system mounted on a patient 1 and ready for use. The chest compression subsystem 2 comprises the motor box 3, the belt cartridge 4, and the compression belt 5 with left and right portions 5L and 5R. The belt is fastened around the patient with fasteners 6, which may be buckles, Velcro® hook and loop fasteners or other fasteners with sensors to sense when the belt is fastened. Ventilation electrodes 7L and 7R are mounted on the belts in the area of the lower chest, over the diaphragm, placed bilaterally. Bipolar electrodes 8L and 8R (or electrode pairs) may also be placed on the neck, bilaterally, to stimulate the phrenic nerve which courses downwardly through the neck. Defibrillation electrodes 9R and 9L are placed in the right sternum parasaggital location 10 and left rib medial location 11, and they may also be located below the patient, on the spine between the shoulder blades, and on the center of the chest, respectively. These electrodes are also used for establishing the electrical contact needed for EKG sensing. Counterpulsion electrodes 12i and 12s are placed on the skin over the abdominal or rectus muscles, with a line of positive electrodes placed in the superior position and a line of ground electrodes placed in the inferior position. Glottic control electrodes are disposed on electrode patch 13 placed on the neck along the tracheoesophageal groove.

Figure 2:
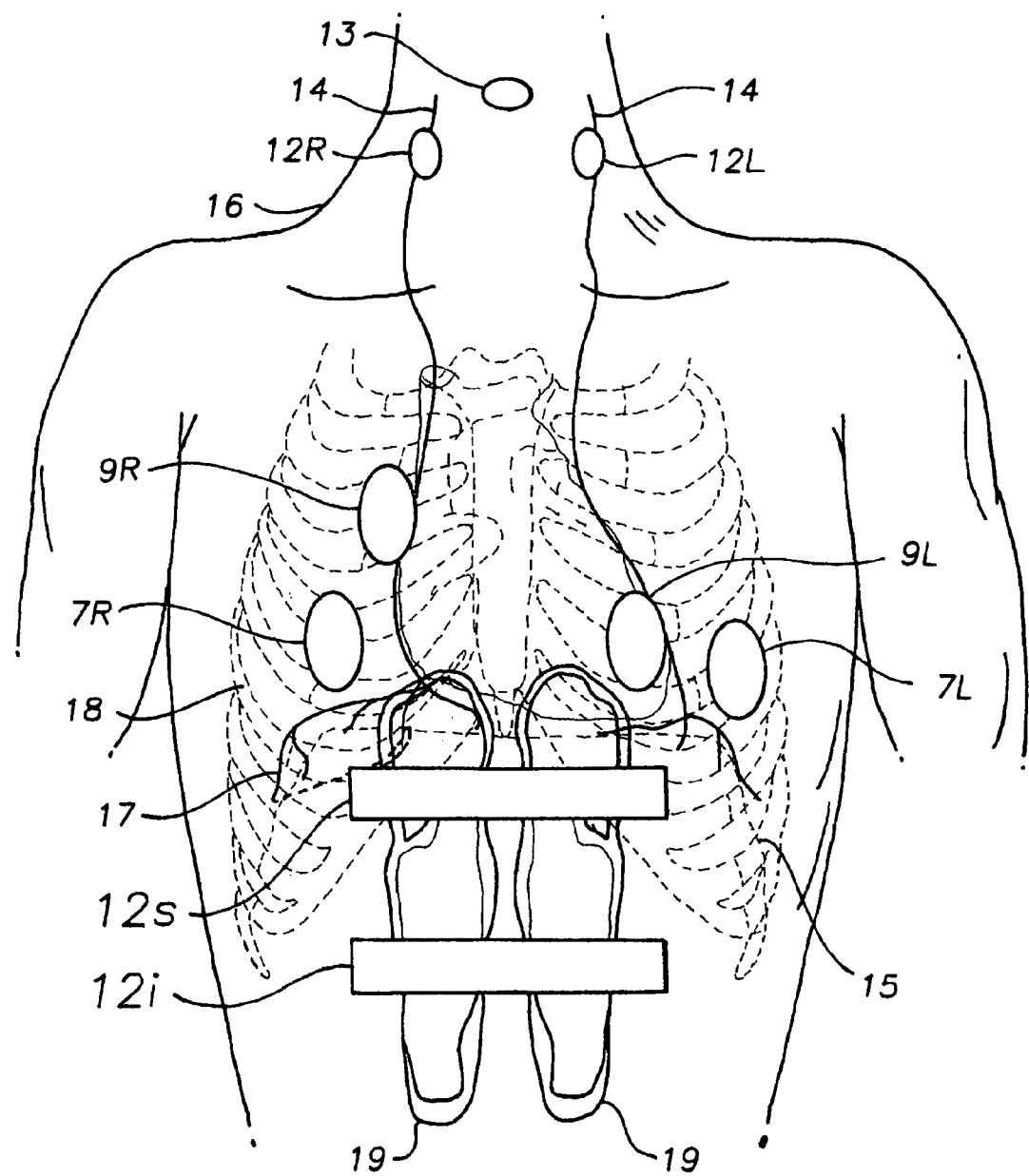
FIG. 2 is diagram of a typical patient illustrating the electrode placement.

FIG. 2 illustrates the nerves of the human body upon which the electro-stimulation system may act. The phrenic nerves 14L and 14R are believed to be used by the body to control the diaphragm 15. The phrenic nerves course from the neck 16, superficially over the scalene muscles, and deep within the chest around the heart to the diaphragm. The phrenic nerves divide into the phrenicoabdominal branches 17. The phrenic nerves comprise both efferent and afferent nerves which run together along their common course. The phrenic nerves and the diaphragm are principal components of breathing. Other nerves and muscles which are used in breathing are the intercostal nerves, located between the ribs 18 and controlling the external intercostal muscles, and the internal intercostal muscles. The abdominal muscles 19, controlled by intercostal nerves, are used in active breathing. The electrodes 7L and 7R, 8L and 8R, 9L and 9R, 12i and 12s, and 13 are illustrated in the appropriate positions as viewed from the front of the patient.

The airway is controlled by the glottic opening (including the vocal cords) which is controlled by the recurrent laryngeal nerve. The operation of the glottis is not typically impaired in cardiac arrest patients. However, its operation can be influenced by electrical stimulation of the recurrent laryngeal nerves, and closure during the compression period of the CPR device enhances intrathoracic pressure. The recurrent laryngeal nerve may be stimulated with electrical stimulation delivered most conveniently through an electrode mounted on the skin of the neck, along the tracheo-esophageal groove. It may also be activated from inside the throat of the patient by applying electrical stimulation directly to the vocal cords, or through the tracheal wall or the esophageal wall (with electrodes mounted on an ET tube, which is routinely inserted by emergency medical technicians). Stimulation of the RLN will open or close the glottic opening depending on the frequency of the applied electrical stimulus. For transcutaneous stimulation, stimulation at frequencies below 30 Hertz cause the vocal cord to open, while stimulation at frequencies from 40-100 Hertz will cause the vocal cords to close. Stimulation with pulses ranging up to 20 milli-amps and pulses of 0.5 msec to 2 msec duration should be effective to stimulate closure of the glottic opening.

There are two electrical mechanisms that can be used to activate a muscle within the body, and the systems described below can allow for both. First, the motor nerve (such as the phrenic nerve) is used by the body to transmit a nervous system impulse to activating nerves which directly innervate the muscles. The motor nerves may be stimulated by an electrical pulse to cause the motor nerve to stimulate the activating nerves within the muscle to be contracted. Second, the activating nerves that directly innervate the muscles may be locally stimulated to cause muscle contraction. The diaphragm, the intercostal muscles, and the abdominal muscles may be stimulated with both electrical mechanisms.

The CPR device illustrated in FIG. 1 stimulates the motor nerve and the activating nerves, either singly or together, to cause contraction of the diaphragm, the intercostal muscles, and the abdominal muscles. The diaphragm and the intercostal muscles are stimulated in coordination with the compression mechanism to cause those muscles to cause an inhalation. The abdominal muscles are stimulated in coordination with the compression mechanism to make those muscles contract. The contraction of the abdominal muscles results in a binding of the abdomen that, when syncopated with chest compressions provides an electrically induced version of counterpulsion which increases the effectiveness of the chest compression mechanism in creating blood flow within a patient.

The manner in which electrical stimulation may be applied may vary considerably and yet still provide effective activation of the muscle groups involved. The electrical stimulation is preferably applied in repeated bursts comprising a number of pulses. The pulses are characterized by their pulse width and pulse amplitude (current or voltage). The pulse bursts, or pulse trains, may be characterized by the pulse train width and the number of pulse bursts per second. In each instance, the pulses employed may be monophasic, biphasic, or polyphasic, according to medical indications at the time of use. The pulses may be DC pulses or AC pulses of varying frequency.

For stimulation of the respiratory muscles, we prefer an electrical pulse pattern which causes a smooth inhalation. The respiratory stimulation is provided through the electrodes 8L and 8R on the neck or electrodes 7L and 7R over the general area of the diaphragm. When electrical stimulation is supplied through the chest electrodes, the electrical stimulation may be provided in single amplitude pulse trains containing numerous pulses of 0.03 msec pulse width, delivered at 60 pulses per second, delivered at amplitude up to one amp. Preferably, a linearly ramped pulse train with an initial amplitude of about 10-50 milli-amps and a final amplitude of about 100-200 milli-amps, with pulse widths of 0.01 to 0.1 msec, and 60 pulses per second, with pulse train of 0.5 to 2 seconds. A frequency modulated pulse train may also be used, with a pulse train of about 1 second, individual pulses of 0.01 msec to 0.1 msec, an amplitude of 50-200 milli-amps, with the pulse frequency increasing from 10 pulses per second to 100 pulses per second during the pulse train. These pulse patterns will provide for smooth inhalation and minimal potential for interference with the proper electrical operation of the heart.

For stimulation of the abdominal muscles, electrical stimulation signals are transmitted through the abdominal electrodes 12$i$ and 12$s$. For the contraction of these muscles, stimulus pulse trains at about 50 Hz, 0.03 msec to 0.2 msec pulse width, and up to 150 volts. The pulse patterns used here may correspond to those used for functional electrical stimulation-induced coughs for paralyzed patients.

Figure 3:
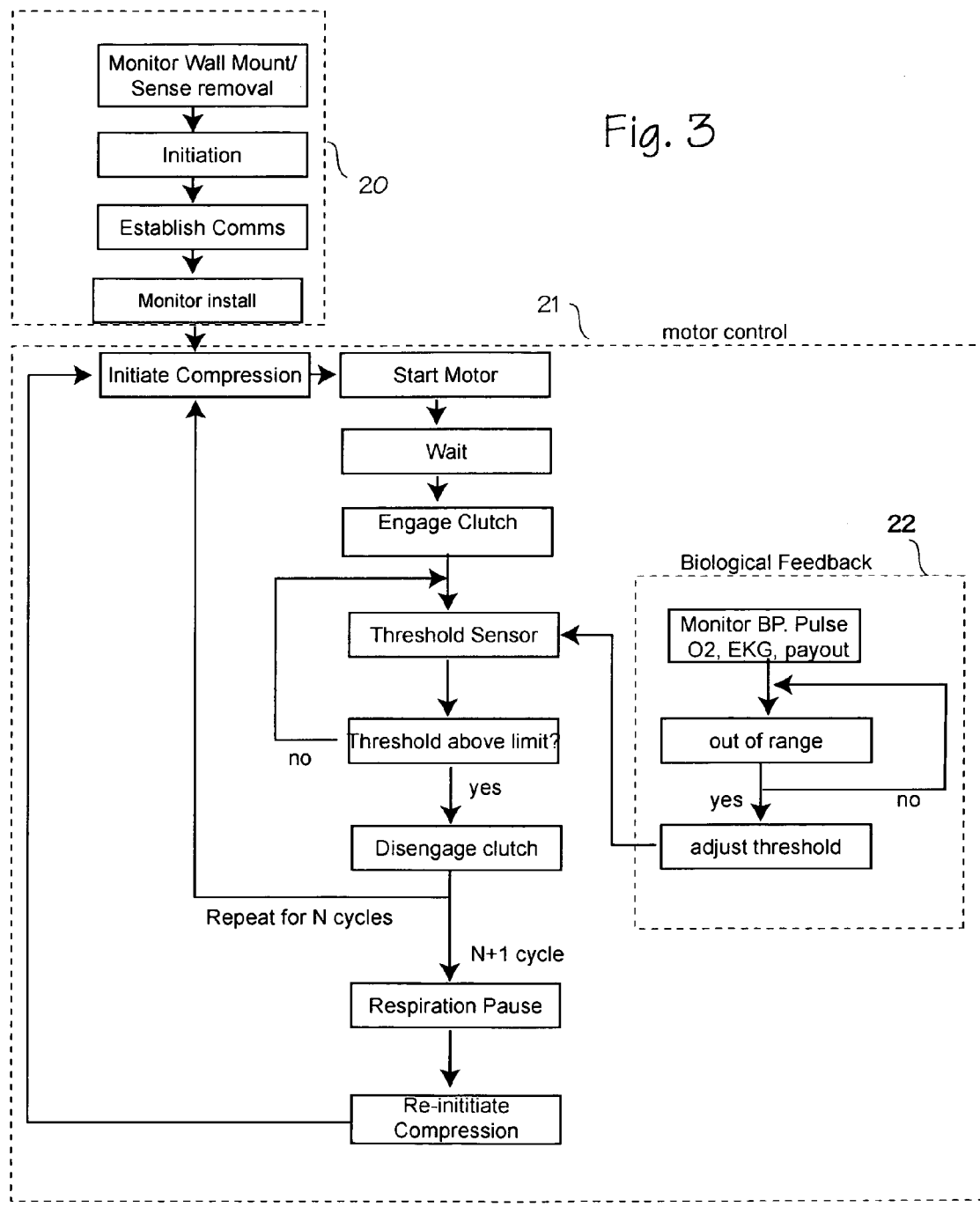
FIG. 3 is a block diagram of the motor control system for use for basic CPR chest compression.

A basic system for chest compression is shown in FIG. 3. Various modules of the motor control system shown in FIG. 3 are the startup and pre-initiation module 20, which operates to monitor the system to detect when a user desires to use the system (sensed, for example, by removal of the device from a storage/charging unit), to initiate or startup the computer controller, to initiate communications with a remote operation center upon initiation of the system, the control unit will monitor installation of the belt via appropriate sensors in the buckles or through other sensors. When the motor control module 21 receives the initiate compression signal from the control unit, the motor is started. The motor in this example is run continuously, and engaged to the belt through a clutch mechanism which is controlled by the control system to repeatedly engage the belt in a take up mechanism and release the belt take up mechanism to cause the desired chest compressions. This cyclic engagement of the clutch continues repeatedly for five cycles, as recommended by current CPR guidelines, and then is interrupted for a respiration pause, if desired. A feedback module 22 monitors system parameters or patient biophysical parameters used by the system to control its operation. For example, to avoid excessive drain on the batteries, the motor controller includes a torque sensor (sensing current supply to the motor, for example) and a belt length sensor, and monitors the torque or load on the motor. A threshold for chest compression is established above which further compression is not desired or useful, and if this occurs during the nominal period of clutch engagement, then the clutch is disengaged and the cycle continues. The system also monitors biophysical parameters such as Blood pressure, pulse, blood oxygen levels, EKG signals, end-tidal CO2, etc. and if found insufficient the system may adjust the maximum allowed compression, the pace of compression, or other parameters. The cycle time and period, number of cycles between respiration pauses, and the compression limit, can be set according to current guidelines, and can also be varied by the remote medical personnel via the remote control capabilities of the control unit. As indicated, after a predetermined number of cycles N (usually five compressions), the system will pause for a few seconds to allow for effective ventilation, which may be accomplished with a bag mask, mouth-to-mouth, or through the electroventilation described in this patent.

To provide for electro-stimulus including electro-counterpulsion, electroventilation, or synchronized cardioverting shock in the system, the system must be enabled to do so. By "enabled," we mean that the system must be told that it is permitted to initiate electro-stimulus before it does so. The system may be provided as a dumb automated system, a controlled system, or a smart automated system, depending on the type of electro-stimulus, and the prevailing medical preferences.

For control of counterpulsion electro-stimulus in a dumb automated system, the counterpulsion electro-stimulus may be enabled at all times, while in a controlled automated system, the counterpulsion electro-stimulus will be enabled when the by-stander operator provides input to the system, or when the remote expert medical staff remotely enables it. In a smart automated system, the counterpulsion electro-stimulus will be enabled when the system senses a biological parameter for which counterpulsion is medically indicated and automatically stopped when the sensed biological parameter indicates that counterpulsion electro-stimulus is no longer indicated. While the condition for which counterpulsion is medically indicated will vary as the ACLS is modified over time as we gain clinical experience which indicates the optimal conditions for counterpulsion and potential risk conditions (during which counterpulsion is counterindicated), we currently consider all cardiac arrest conditions to be a condition which is an indication for counterpulsion. This condition may be sensed with EKG sensors, blood pressure sensors and pulse amplitude sensors, and feedback from these sensors may be provided to the control system for consideration by the system.

For control of electro-ventilation in a dumb automated system, the electro-ventilation stimulus may be enabled at all times, while in a controlled automated system, the electro-ventilation will be enabled when the by-stander operator provides input to the system, or when the remote expert medical staff remotely enables it. In a smart automated system, the electro-ventilation stimulus will be enabled when the system senses a biological parameter for which electro-ventilation is medically indicated and automatically stopped when the sensed biological parameter indicates that electro-ventilation stimulus is no longer indicated. While the condition for which electro-ventilation is medically indicated will vary as the ACLS is modified over time and as we gain clinical experience which indicates the optimal conditions for electro-ventilation and potential risk conditions (during which electro-ventilation is counterindicated), we currently consider respiratory arrest to be a condition for which electro-ventilation is indicated. This condition may be sensed with $CO_2$ sensors, air flow sensors, air temperature sensors, and chest mounted impedance sensors, and feedback from these sensors may be provided to the control system for consideration by the system.

Control of cardioverting shock in a dumb automated system may seem undesirable in field applications, but may prove quite useful in hospital and emergency room settings. Thus, a dumb automatic system in which the cardioverting shock stimulus may be enabled at all times may be operated. Cardioverting shock is more likely to be successful when applied to a compressed heart, as is known by surgeons who practice open heart surgery. To take advantage of this fact, the device may be provided in an embodiment in which it compresses the chest and applies cardioverting shock near the end of the compression period. This embodiment initiates a compression cycle when instructed to do so by the operator, and automatically applies the cardioverting shock to the patient at the optimum time near the end of the compression cycle. Additionally, because cardioverting shock is more likely to succeed when applied after a period of CPR, the automatic embodiment can optionally perform CPR (and electroventilation) for a number of compression cycles, after which it automatically applies the cardioverting shock to the patient. In a dumb automated system, the cardioverting shock is applied automatically after the compression strokes, without regard to further operator input (except for shutdown), and without regard to biological parameters. After the cardioverting shock is applied, the operators can reassess the patient to determine if the heart has been successfully defibrillated, and apply additionally cardioverting shocks according to accepted protocols such as the ACLS.

The system can be programmed to apply cardioverting shock while in a controlled automated mode. The cardioverting shock will be enabled when the by-stander operator provides input to the system, or when the remote expert medical staff remotely enables it. The system can be programmed to apply cardioverting shock while in a smart automated mode. In a smart automated system, the cardioverting shock will be enabled when the system senses a biological parameter for which cardioverting shock is medically indicated and automatically stopped when the sensed biological parameter indicates that cardioverting shock stimulus is no longer indicated. It is clearly not desired under current ACLS guidelines to periodically defibrillate a cardiac arrest patient, so the smart automatic system will preferably use EKG signal input to determine when defibrillation is required, and when it has been successful or unsuccessful. The system is programmed to perform CPR, simultaneously assess the need for defibrillation, apply the cardioverting shock, assess the success of the cardioverting shock in defibrillating the patient, and follow up with additional application of CPR if defibrillation has been unsuccessful or terminate CPR if defibrillation has been successful in restoring normal heart rhythm and blood flow. The system can continue to monitor the patient EKG'S, blood pressure and pulse in case of a recurrence of the fibrillation, a non-perfusing rhythm or a cessation of blood flow, in which case it is programmed to re-initiate CPR. While the condition for which cardioverting shock is medically indicated will vary as the ACLS is modified over time as we gain clinical experience which indicates the optimal conditions for cardioverting shock and potential risk conditions (during which cardioverting shock is counterindicated), we currently consider ventricular fibrillation and ventricular tachycardia to be a conditions which are indications for cardioverting shock. These conditions may be sensed with the chest mounted EKG electrodes and acoustic sensors, and feedback from these sensors may be provided to the control system for consideration by the system. Commercially available sensors, electrodes and EKG analysis systems such as the ForeRunner™ AED sold by HP Heartstream can be used as the basis for the cardioverting subsystem.

Figure 4A:
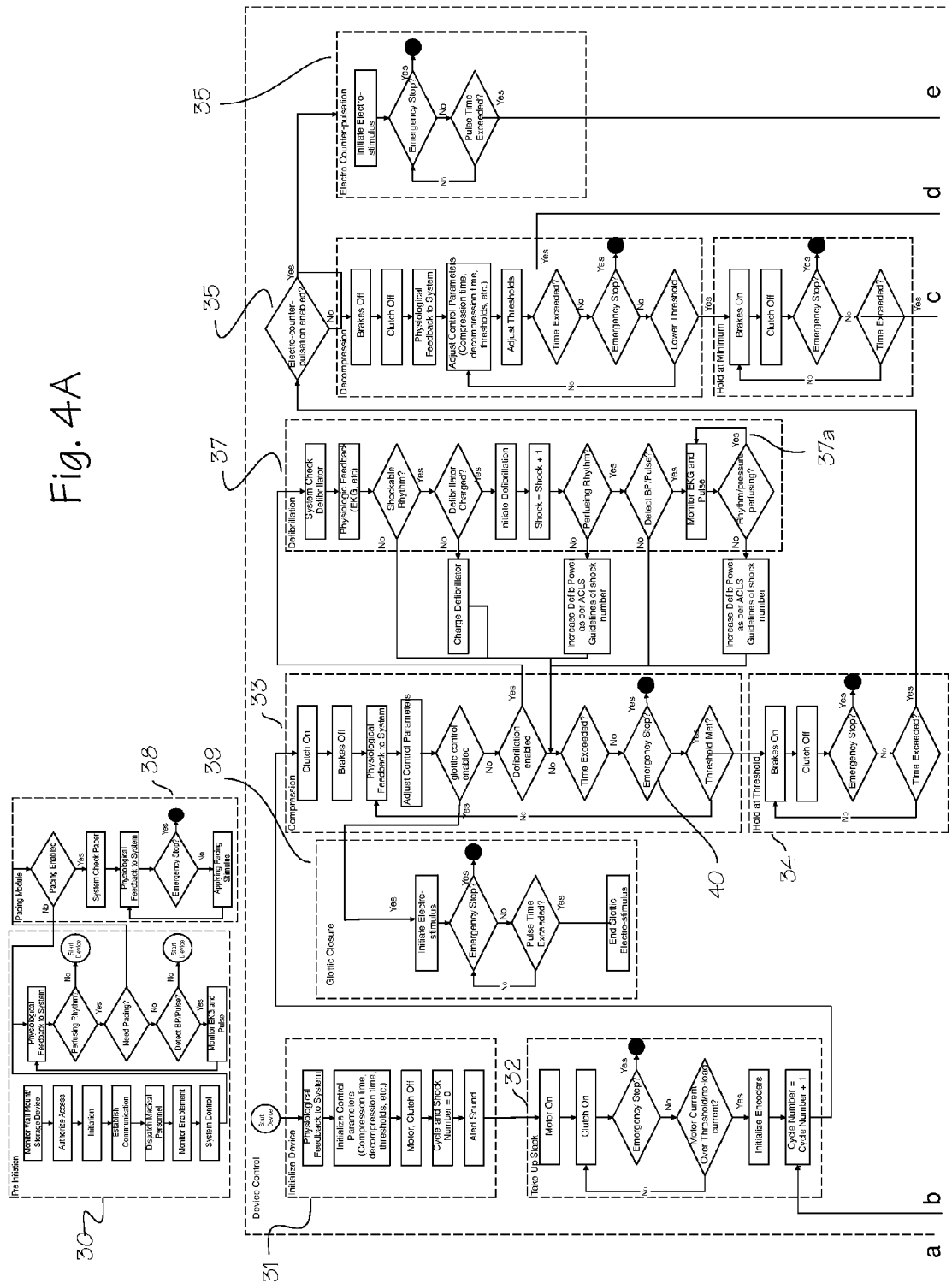
FIG. 4A and FIG. 4B are a block diagram of the motor control system for use in electro-ventilation during respiration pauses of the compression system, for use in electro-counterpulsion during operation of the compression system, and for use in the synchronized cardioverting shock system.
Figure 4B:
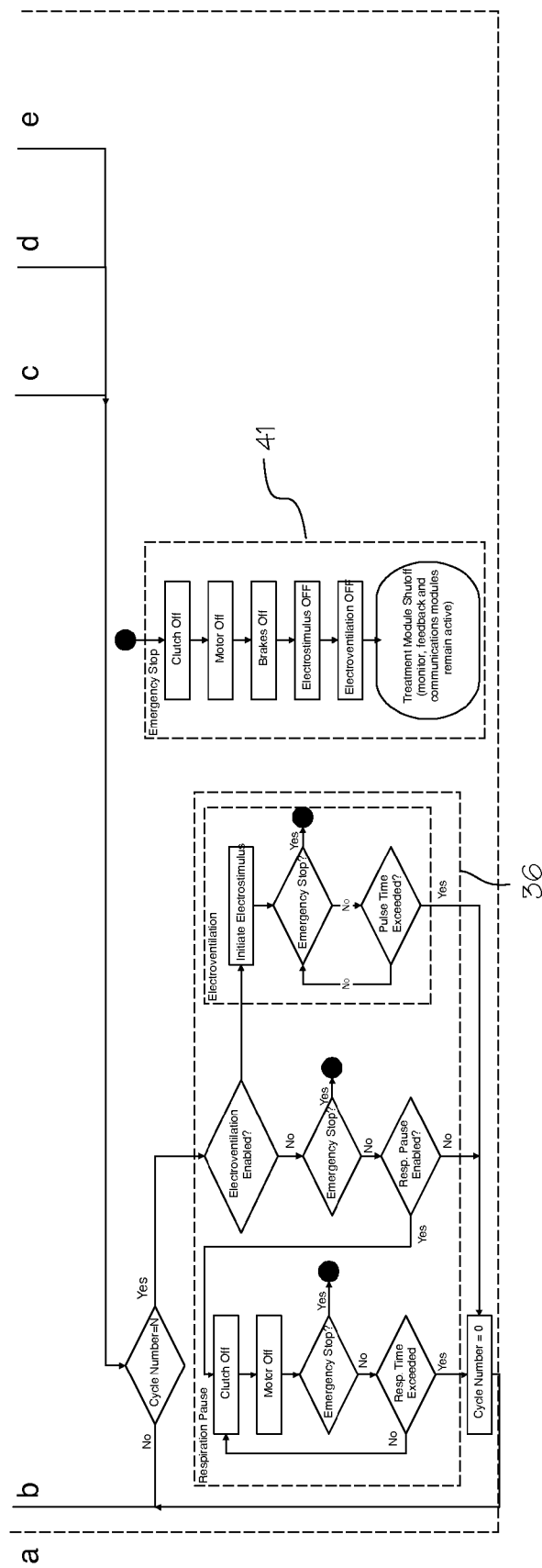

FIG. 4 is a block diagram of the system software in the form of a flow chart, illustrating the programming of the system which enables it to accomplish CPR with integrated electro-counterpulsion, electroventilation and defibrillation. The pre-initiation module 30 operates to monitor the system to detect when a user desires to use the system (again, by sensing removal of the device from a storage/charging unit), to initiate or startup the computer controller, to initiate communications with a remote operation center. Additional features such as authorizing access to pre-trained bystanders, automatically alerting emergency medical personnel to the event, and establishing enablement limits may be performed. For instance, it may be advisable to permit electroventilation and electro-counterpulsion to be performed automatically by the system when accessed by moderately trained bystanders, and permit automatic defibrillation only when the system is accessed by highly trained bystanders, emergency medical technicians, nurses or doctors. In the system initialization module 31, the system software directs the system to check physiological feedback, initialize the control parameters, ensure that the motor is off, the clutch is off and the system counter, if the system is fitted with a counter, is set at zero for the number of compressions and number of cardioverting shocks. The slack take-up module 32 directs the system to spool the belt to a point where it is not slack around the patient, and record system parameters such as belt deployment length and initialize encoders used to track the amount of chest compression provided. The compression module 33 controls the system to repeatedly compress the chest with the mechanisms of the chest compressing mechanism, which in our system are described in detail in our co-pending U.S. patent application Ser. No. 09/087,299 (now U.S. Pat. No. 6,066,106) and application Ser. No. 08/922,723 (now U.S. Pat. No. 6,142,962). The "hold at compression" module 34 controls the system to maintain a period of static compression after each compression, if desired.

To provide for counterpulsion in this exemplary system, the system is designed to transmit a stimulating pulse to the intercostal nerves innervating the abdominal muscles when the compression stroke is complete. Thus, each time the clutch disengages, the system checks to see if counterpulsion is enabled and, if so, it initiates a counterpulsion stimulus, as indicated by the electro-counterpulsion module 35 placement after each compression and/or static compression period. Thus, after each hold period, which signifies the end of the compression stroke and the end of each hold period, the system instructs the electro-stimulation system to stimulate the abdominal muscles to cause the counterpulsion that results from contraction of the abdominal muscles. The counterpulsion may be initiated immediately following the compression stroke, shortly before the end of the compression cycle, or shortly after the end of the compression cycles, or at any time between compression cycles. Clutch disengagement is used as the proxy for the end of the compression period in this system, but any other system parameter may be used as a proxy for the end of the compression period. For example, motor status, brake status, pneumatic valve status (for pneumatic systems), drive piston status (for Thumper® type devices), or other actual parameters may be used. The system controller is programmed to activate the counterpulsion electro-stimulus in tandem with the proxy action. In other words, the system, if programmed to disengage the clutch to end the compression period, initiates clutch disengagement and initiates the counterpulsion electro-stimulation at or about the same time. (If desired, the actual status of the proxy action may be monitored by the system, and the actual status used by the system as the signal to initiate the counterpulsion electro-stimulus. The actual status may also be checked by the system and used as a double-check on the system status before initiation of the counterpulsion electro-stimulus, and in this manner the possibility that counterpulsion will be initiated during a sub-optimal portion of the chest compression/relaxation cycles is reduced.)

It may be advantageous to stimulate the abdominal muscles into contraction at varying points in the compression cycle. Abdominal binding may be affected by applying the electro-stimulus pulse to the abdominal muscles near the beginning of the chest compression. If this is desired, the electro-counterpulsion module may be reconfigured to act as an abdominal binding module, and it may be referred to at the start of the compression module operation, and the required electro-stimulus can be applied while the compressive force is being applied to the chest.

To provide for electroventilation in this exemplary system, the system is designed to transmit a stimulating pulse to the phrenic nerve when the compression stroke is complete. Thus, each time the system counts a number of compressions desired between respiration pauses, the system initiates an electroventilation stimulus, as indicated by the electroventilation module 36 placement after every group of N compressions and during each respiration pause. Thus, during each respiration pause, the system checks to determine if electroventilation is enabled, and if so, it instructs the electroventilation system to stimulate the phrenic nerve or the phrenico-abdominal branches (nerves directly innervating the diaphragm) to cause the electroventilation that results from contraction of the diaphragm muscles. The intercostal nerves may also be stimulated to activate the intercostal muscles.

The block diagram for automatic defibrillation is also illustrated in FIG. 4. The system incorporates an automatic external defibrillator which is tied into the operation of the chest compression device. The defibrillation module 37 may incorporate any available automatic defibrillation algorithm to determine if the EKG signals sensed by the EKG electrodes constitute a shockable rhythm (a rhythm indicating that a defibrillating shock can be expected to result in cardioversion and return of normal sinus rhythm to the heart). The defibrillation module is referred to at or near the end of each active compression stroke if defibrillation has been enabled. Defibrillation may be enabled in all cases, in situations where a highly trained bystander has accessed the system, or where the system has established communication with a remote medical center which, through the communication system, has enabled the defibrillation system. The system may place limits on when the defibrillation module can be enabled, such as requiring a period of one to two minutes of chest compression prior to allowing application of defibrillation of shock. The defibrillation module is referred to near the end of an active compression, so that the defibrillation shock can be delivered while the heart is in a relative state of compression. The defibrillation module accepts feedback from installed EKG sensing electrodes and blood pressure sensors, and may adjust the defibrillation power according to current ACLS protocols. If the defibrillation system detects normal or effective EKG signals and effective blood pressure or pulse, it may then communicate to the control system or refer the system to the emergency stop module. As shown in module 37, the decision loop 37a will maintain the system in a holding status by referring the system back to the EKG/blood pulse monitoring sub-module continuously until the sensed signals indicate that spontaneous blood flow has failed. Failure may be indicated either by absence of proper EKG signals, indicating a non-perfusing heart rhythm, or by absence of blood pulse or blood pressure in the presence of otherwise perfusing rhythm. Thus the system is capable of detecting the condition of electromechanical disassociation, in which the electrical activity of the heart appears normal but proper mechanical pumping action has not been restored, and the system can continue compression after detecting this situation. (Although there appears to be little danger in compressing the chest of a revived or healthy patient, preservation of system power, patient comfort, and bystander notification will be enhanced by preventing the system from compressing/electro-stimulating a revived patient.)

The block diagram for cardiac pacing is also illustrated in FIG. 4. The system used for delivery of defibrillation stimulus may be used also for cardiac pacing, and is also tied into the operation of the chest compression device. The pacing module 38 may incorporate any available pacing algorithm to determine if the EKG signals sensed by the EKG electrodes indicate the need for pacing. Currently, bradycardia (an excessively slow heart beat) is considered the primary indication for pacing. The pacing module is referred to in the pre-initiation stage because it is expected that bradycardia can be treated with pacing alone, and delay of compression saves battery power in the event that the patient's condition degrades to the point where compression is required. The pacing module periodically refers to the EKG monitoring system to determine the continuing need for pacing, or the need to move onto the device control module for compression and other electro-stimulus. (The pacing module may also be programmed to operate in tandem with the compression cycles of the chest compression device, in which case it is referred to at or near the end of each active compression stroke, so that the pacing shock can be delivered while the heart is in a relative state of compression.)

Pacing may be enabled in all cases, in situations where a highly trained bystander has accessed the system, or where the system has established communication with a remote medical center which, through the communication system, has enabled the pacing system. The system may place limits on when the pacing module can be enabled, such as requiring a period of one to two minutes of chest compression prior to allowing application of pacing of shock. The pacing module accepts feedback from installed EKG sensing electrodes and blood pressure sensors, and may adjust the pacing power or timing within the compression cycles.

The block diagram for automatic glottic stimulation is also illustrated in FIG. 4. The system incorporates an automatic external recurrent laryngeal nerve stimulator which is tied into the operation of the chest compression device. The glottic pacing module 39 may be referred to at or near the beginning of each active compression stroke to close the glottic opening. The system checks to determine if the glottic opening control has been enabled, and, if so, initiates the delivery of electrical stimulation at the closing frequency. Thus, just before each compression period (depending on medical indications at the time of use), the system instructs the electro-stimulation system to stimulate the recurrent laryngeal nerve to cause the glottis to close. The stimulus is removed after each compression, as illustrated in this system. However, the stimulus may be applied for the duration of the N compressions between respiration pauses if medically indicated.

Throughout the block diagram of FIG. 4, the system checks for input of a stop signal. A stop signal may be communicated from a control panel by the bystander operating the device, or by remote medical personnel, or by automatic operation of the system. Each subroutine and active module of the device (that is, modules which can instruct and operate the system to apply mechanical or electrical power to the patient) is provided with an emergency stop feature wherein each active module is programmed to check for a stop signal prior to applying mechanical or electrical power to the patient. Each active module may also rely on its referring module for checking the stop signal. For example, the compression module 33 initiates its first compression relying upon the stop signal check performed in the slack take-up module 32 prior to reference from the slack take-up module 32 to the compression module. Thereafter, the compression module relies upon emergency stop check 40 within the compression module.

Upon sensing an emergency stop signal, the system refers to the emergency stop module 41. The emergency stop module then operates the system to put it into a safe condition. This includes operating the mechanical system to release compression of the body by turning off the system or controlling operation of the system to pay out the compression belt so that it exerts little or no force on the body, then disabling further compression. It also includes disabling or turning off the electroventilation, electro-counterpulsion, and defibrillation modules so that they will not apply electrical stimulation to the body. The shut down preferably maintains sensing, communications, display and system initiation modules in operation so that the bystanders may determine the status of the patient, and possibly re-initiate compression if needed.

Several of the control system modules depend on sensed electrical signals from the patient or from the compression device. However, the power required for defibrillation, electro-stimulus of the respiratory system, and pacing represent electrical surges of significant power relative to the sensing systems. For this reason, the feedback devices used to provide information to the system should be protected with circuitry which isolates the necessary signal processing systems from electrical signals with voltage or current far in excess of the expected feedback signals.

The term electro-stimulation system may refer to a system that stimulates the vagal nerve at any point, the phrenic nerve at any point, the abdominal muscle nerves, or the heart from any point on or within the body. The electrical pulse generator may provide a pulse intended to stimulate a nerve which controls a muscle or muscle group (as with the phrenic nerves) or it may be intended to affect the electrical activity of the heart (as with a pacing stimulus or a cardioverting shock). The chest compression device used may be the circumferential belt and the drive system illustrated in our patents, such as U.S. Pat. No. 6,066,106, or our co-pending patent applications, such as application Ser. No. 09/345,645 (now U.S. Pat. No. 6,398,745) and Ser. No. 09/866,377 (now U.S. Pat. No. 6,616,620), or the compression device may be a pneumatic bladder, a reciprocating piston or other system. In this case, the block diagram of FIG. 4 can readily be adapted to control those mechanisms, and the complimentary electro-stimulation modules can be controlled in coordination with the particular mechanical system used.

It is not necessary that the chest compression device actually exert a force on the chest to expand the chest. It is sufficient for the device to cause expansion of the chest by releasing the compression force exerted on the chest during the compression portion of the cycle, thereby permitting the natural elasticity of the thoracic cavity to lead to chest expansion. However, systems providing active compression/decompression, which actually exert a force on the chest to expand the chest (usually a suction force) may also be incorporated into the system.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device for compressing the chest of a patient comprising:
   a chest compression device capable of repeatedly compressing the chest of the patient and causing or allowing the chest to expand;
   an electro-stimulation system comprising an electrode attached to the patient and an electrical stimulation generator operably connected to the electrode, said electrical stimulation generator being capable of generating electrical energy and transmitting said energy to the electrode;
   a controller for controlling the chest compression device and the electro-stimulation system, said controller programmed to coordinate the operation of the chest compression device with the operation of the electro-stimulation system so that the electro-stimulation system transmits electrical energy to the electrode after CPR is performed for a number of compression cycles during periods of time when the chest compression device is causing or allowing the chest to compress for a period of static compression.

2. The device of claim 1, further comprising at least one feedback device operably connected to the patient, wherein said feedback device comprises a sensor, an electrical signal generator arid a signal transmitter, and said feedback device senses at least one biological parameter of the patient, generates a corresponding electrical signal, and transmits the corresponding signal to the controller, and wherein the controller is programmed to adjust the operation of the electro-stimulation system on the basis of the sensed feedback.

3. The device of claim 2, wherein said feedback device comprises a protection circuit for protecting the feedback device from the electrical energy applied by the electro-stimulation system.

4. The device of claim 1, wherein the controller is capable of receiving a stop signal input signifying a command to cease chest compression and electro-stimulation, and said controller is programmed to check for a stop signal before each cycle of chest compression and before each transmission of electrical energy to the electrode.

5. A device for resuscitating a patient having a chest comprising:
   compressing means for repeatedly compressing, holding and decompressing the chest of the patient;
   defibrillating means for applying the defibrillating stimulus to the patient;
   sensing means for assessing the need for defibrillation of the patient and the success of defibrillating stimulus in defibrillating the patient;
   control means for controlling the operation of the compressing means, the sensing means, and the defibrillating means, said control means to assess the need for defibrillation, perform CPR for a predetermined number of compression cycles and apply a defibrillating stimulus to the patient after the predetermined number of compression cycles when the patient's chest is in a compressed hold, and continue repeatedly compressing, holding and decompressing the chest if defibrillation has been unsuccessful or stop compressing the patient if defibrillation has been successful.

6. The device of claim 5, wherein the controller is capable of receiving a stop signal input signifying a command to cease chest compression and defibrillation, and said controller is programmed to check for a stop signal before each cycle of chest compression and before each application of a defibrillating stimulus to the patient.

7. A device for resuscitating a patient having a chest comprising:
   compressing means for repeatedly compressing, holding and decompressing the chest;
   defibrillating means for applying the defibrillating stimulus to the patient;
   sensing means for determining if the patient exhibits a non-perfusing rhythm, electro-mechanical disassociation, or normal cardiac function;
   control means for controlling the operation of the compressing means and the defibrillation means in response to the sensing means, said control means being capable of causing the compressing means to compress the patient when the sensing means determines that the patient exhibits a non-perfusing rhythm or electro-mechanical disassociation, said control means being capable of causing the defibrillating means to apply a defibrillating stimulus to the patient when the sensing means determines that the patient exhibits a non-perfusing rhythm, and said control means being capable of causing the defibrillation means to apply the defibrillating stimulus to the patient when the chest is in a compressed hold.

8. The device of claim 7 wherein the sensing means further comprises:
   means for sensing the electrical activity of the patient's heart and determining if the heart electrical activity proceeds in a perfusing rhythm, means for sensing the flow of blood within the patient to determine if the heart operates in the perfusing rhythm, and means for comparing the sensed electrical activity with the sensed blood flow to determine if the heart is effectively pumping blood;
   and the control means is further capable of causing the compressing means to compress the patient when the electrical activity of the patient's heart indicates appropriate perfusing rhythm but the sensed blood flow indicates that the heart is not operating in perfusing rhythm, and said control means being further capable of causing the defibrillating means to apply a defibrillating stimulus to the patient when the electrical activity of the patient's heart indicates a non-perfusing rhythm.

9. The device of claim 8, wherein the controller is capable of receiving a stop signal input signifying a command to cease chest compression and defibrillation, and said controller is programmed to check for a stop signal before each cycle of chest compression and before each application of a defibrillating stimulus to the patient.

10. The device of claim 7, wherein the controller is capable of receiving a stop signal input signifying a command to cease chest compression and defibrillation, and said controller is programmed to check for a stop signal before each cycle of chest compression and before each application of a defibrillating stimulus to the patient.

* * * * *